(12) United States Patent
Drechsler et al.

(10) Patent No.: US 11,602,750 B2
(45) Date of Patent: Mar. 14, 2023

(54) CUSTOMIZABLE SAMPLE PROCESSING DEVICE

(71) Applicant: Roche Molecular Systems, Inc., Pleasanton, CA (US)

(72) Inventors: Thomas Drechsler, Pleasanton, CA (US); Nancy Schoenbrunner, Pleasanton, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 572 days.

(21) Appl. No.: 15/989,814

(22) Filed: May 25, 2018

(65) Prior Publication Data

US 2018/0345275 A1    Dec. 6, 2018

Related U.S. Application Data

(60) Provisional application No. 62/512,537, filed on May 30, 2017.

(51) Int. Cl.
| | |
|---|---|
| *B01L 3/02* | (2006.01) |
| *B01L 3/00* | (2006.01) |
| *B01L 7/00* | (2006.01) |
| *C12Q 1/6844* | (2018.01) |

(52) U.S. Cl.
CPC .............. *B01L 3/508* (2013.01); *B01L 3/502* (2013.01); *B01L 7/525* (2013.01); *B01L 2200/026* (2013.01); *B01L 2200/0668* (2013.01); *B01L 2200/10* (2013.01); *B01L 2200/16* (2013.01); *B01L 2300/044* (2013.01); *B01L 2300/049* (2013.01); *B01L 2300/087* (2013.01); *B01L 2300/0832* (2013.01); *B01L 2300/123* (2013.01); *B01L 2400/0481* (2013.01); *B01L 2400/06* (2013.01); *B01L 2400/0655* (2013.01); *C12Q 1/6844* (2013.01)

(58) Field of Classification Search
CPC ....... B01L 2300/044; B01L 2300/0832; B01L 2300/06
See application file for complete search history.

(56) References Cited

U.S. PATENT DOCUMENTS

| | | | | |
|---|---|---|---|---|
| 7,718,421 | B2* | 5/2010 | Chen ........................ | G01N 1/10 435/304.2 |
| 9,708,599 | B2* | 7/2017 | Chen ........................ | B01L 3/502 |
| 10,369,572 | B2* | 8/2019 | Marion, Jr. .............. | B01L 3/523 |
| 10,774,393 | B2* | 9/2020 | Lu ............................ | C12Q 1/701 |
| 2004/0023207 | A1* | 2/2004 | Polansky ............... | A61K 48/005 435/5 |
| 2004/0161788 | A1* | 8/2004 | Chen ..................... | G01N 33/543 435/6.16 |
| 2006/0178644 | A1* | 8/2006 | Reynolds ........... | A61M 5/31511 604/232 |
| 2009/0011417 | A1 | 1/2009 | Maltezos et al. | |
| 2013/0217026 | A1* | 8/2013 | Egan ........................ | B01L 7/52 435/6.12 |
| 2014/0356941 | A1 | 12/2014 | Bransky et al. | |
| 2015/0105300 | A1* | 4/2015 | Chen ................... | C12N 15/1003 422/549 |
| 2016/0033412 | A1 | 2/2016 | Tan et al. | |
| 2016/0346779 | A1* | 12/2016 | Ettlin ..................... | B01L 3/5029 |
| 2017/0176302 | A1* | 6/2017 | Bearinger ................ | G01N 1/38 |
| 2019/0201903 | A1* | 7/2019 | Douglas ............ | B01L 3/502715 |
| 2020/0121910 | A1* | 4/2020 | Grant ....................... | A61L 2/26 |

FOREIGN PATENT DOCUMENTS

| | | | | |
|---|---|---|---|---|
| EP | | 1106250 A2 | 6/2001 | |
| WO | WO-2004080597 A2 * | | 9/2004 | .............. B01L 3/502 |
| WO | | 2007100500 A2 | 9/2007 | |
| WO | WO-2008076395 A2 * | | 6/2008 | ........ B01L 3/502715 |
| WO | WO-2009011942 A2 * | | 1/2009 | ........ B01L 3/502715 |

OTHER PUBLICATIONS

Chen et al., 2010. An integrated, self-contained microfluidic cassette for isolation, amplification, and detection of nucleic acids. Biomedical microdevices, 12(4), pp. 705-719. (Year: 2010).*
International Search Report and Written Opinion dated Jul. 2, 2018 in corresponding PCT/EP2018/064168 filed on May 30, 2018, pp. 1-12.

* cited by examiner

*Primary Examiner* — Gary Benzion
*Assistant Examiner* — Olayinka A Oyeyemi
(74) *Attorney, Agent, or Firm* — Pamela C. Ancona

(57) ABSTRACT

A sample processing tubule is provided including, from a proximate to a distal end, an opening through which a sample is introducible, at least three segments, and an reagent introduction port operatively connected to a distal segment of the at least three segments. The reagent introduction port enables the addition of a reagent in the distal segment of the tubule, enabling the user to create a customizable assay tubule.

8 Claims, 3 Drawing Sheets

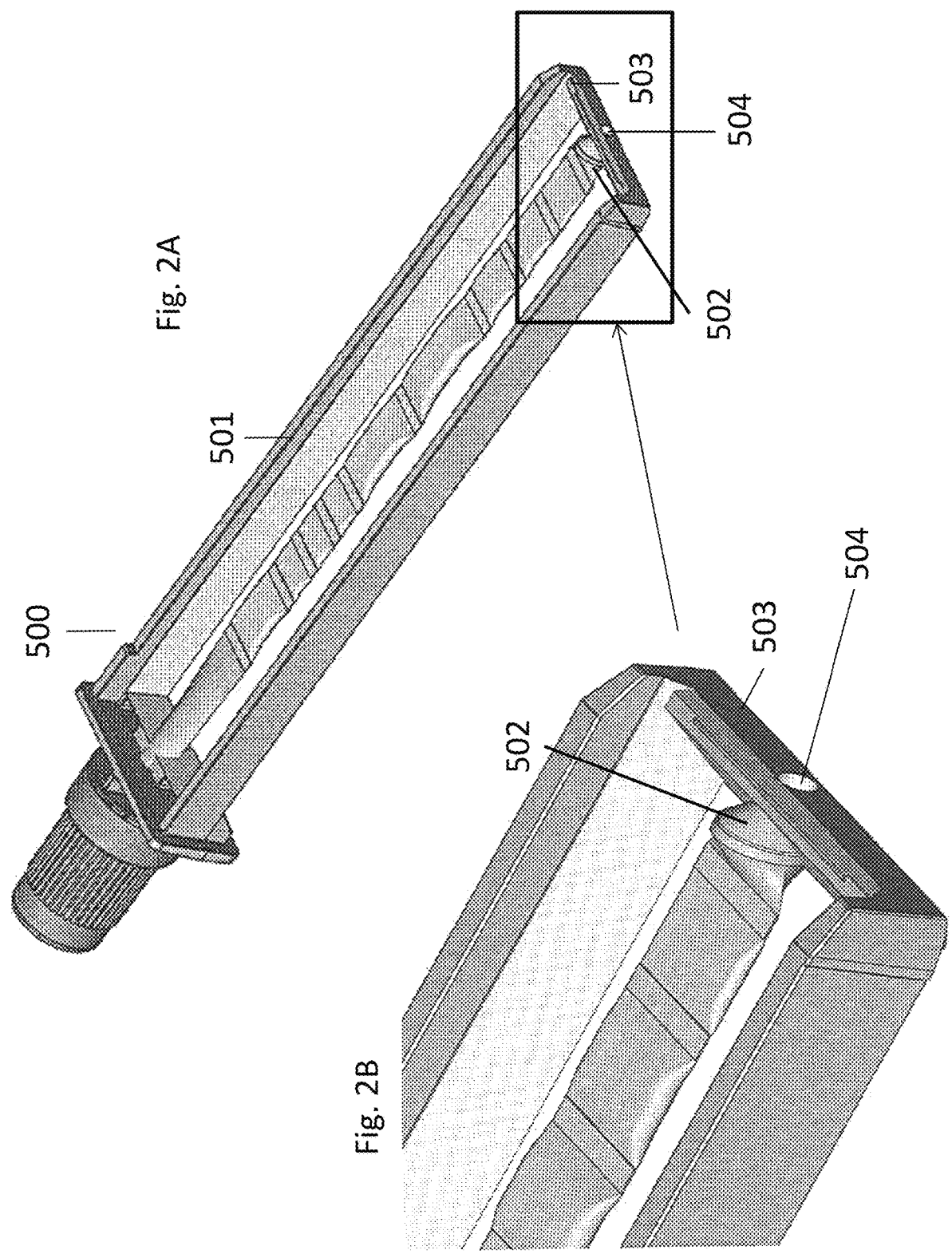

CUSTOMIZABLE SAMPLE PROCESSING DEVICE

CROSS-REFERENCE TO RELATED APPLICATIONS

The present application claims the benefit of priority under 35 U.S.C. § 119(a) of U.S. Provisional Application No. 62/512,537, filed May 30, 2017, the disclosure of which is incorporated herein by reference in its entirety. Reference is also made to the following U.S. Patents and Published Applications: U.S. Pat. Nos. 7,718,421; 6,748,332; 6,780,617; 7,799,521; 6,318,191; 7,337,072; 7,833,489; 8,148,116; 7,935,504; 6,964,862; 6,318,191; 6,748,332; 7,799,521; 8,936,933; 7,785,535; 8,414,845; 2015-0105300; 2013-0040830; and 2012-0276532, as well as U.S. Provisional Application Ser. No. 62/512,516. The disclosures of each of these publications are incorporated herein by reference in their entireties.

BACKGROUND

The analysis of nucleic acids in clinical or environmental samples generally involves a series of chemical, optical, electrical, mechanical, and thermal processing steps on the fluid samples. In recent years, there has been growing interest in developing disposable cartridges for conducting analyses of biological samples for various diagnostic and monitoring purposes. For example, U.S. Pat. No. 5,587,128 to Wilding discloses devices for amplifying a preselected polynucleotide in a sample by conducting a polynucleotide amplification reaction. U.S. Pat. No. 5,922,591 to Anderson et al. describes a miniaturized, integrated nucleic acid diagnostic device and system. The device is generally capable of performing one or more sample acquisition and preparation operations, in combination with one or more sample analysis operations.

Due to the complex series of operations that must be performed using fully integrated, self-contained devices, manufacturers have produced such devices with all of the reagents necessary to perform each operation required for an assay pre-loaded in the device. As a result, the menu of available assays is quite limited and there is a need to enable a user to incorporate user-provided reagents, e.g., primers and probes, so that the available menu of assays can be expanded to meet the wide range of customer needs.

SUMMARY

The present disclosure provides devices and methods for processing samples. The disclosed devices and methods can facilitate the preparation of samples through multiple processing steps.

The disclosure provides a customizable sample processing tubule comprising, from a proximate to a distal end, an opening through which a sample is introducible, at least three segments, and a reagent introduction port fluidly connected to a distal segment of the at least three segments and adapted to enable the introduction and deposition of reagent into at least one of said at least three segments.

Also provided is a method of processing a sample in a tubule as described herein, comprising: introducing a reagent through said reagent introduction port into said at least one segment; introducing sample through said opening; and driving fluid flow from a first segment at the proximate end of said tubule to said distal segment, thereby contacting said sample with one or more reagents positioned in said tubule and/or reaction conditions to transform at least a portion of said sample into a reaction mixture.

In addition, the disclosure contemplates a kit comprising said sample introduction tube of claim 8, and in one or more separate containers, vials, or compartments, a reagent insertion mechanism, and instructions for use.

BRIEF DESCRIPTION OF THE DRAWINGS

FIG. 2A is a cross sectional view of a sample tube including a tubule, a frame, and an reagent introduction port.

FIG. 2B is an enlarged view of the reagent introduction port.

DETAILED DESCRIPTION

Figures 1A, 1B:
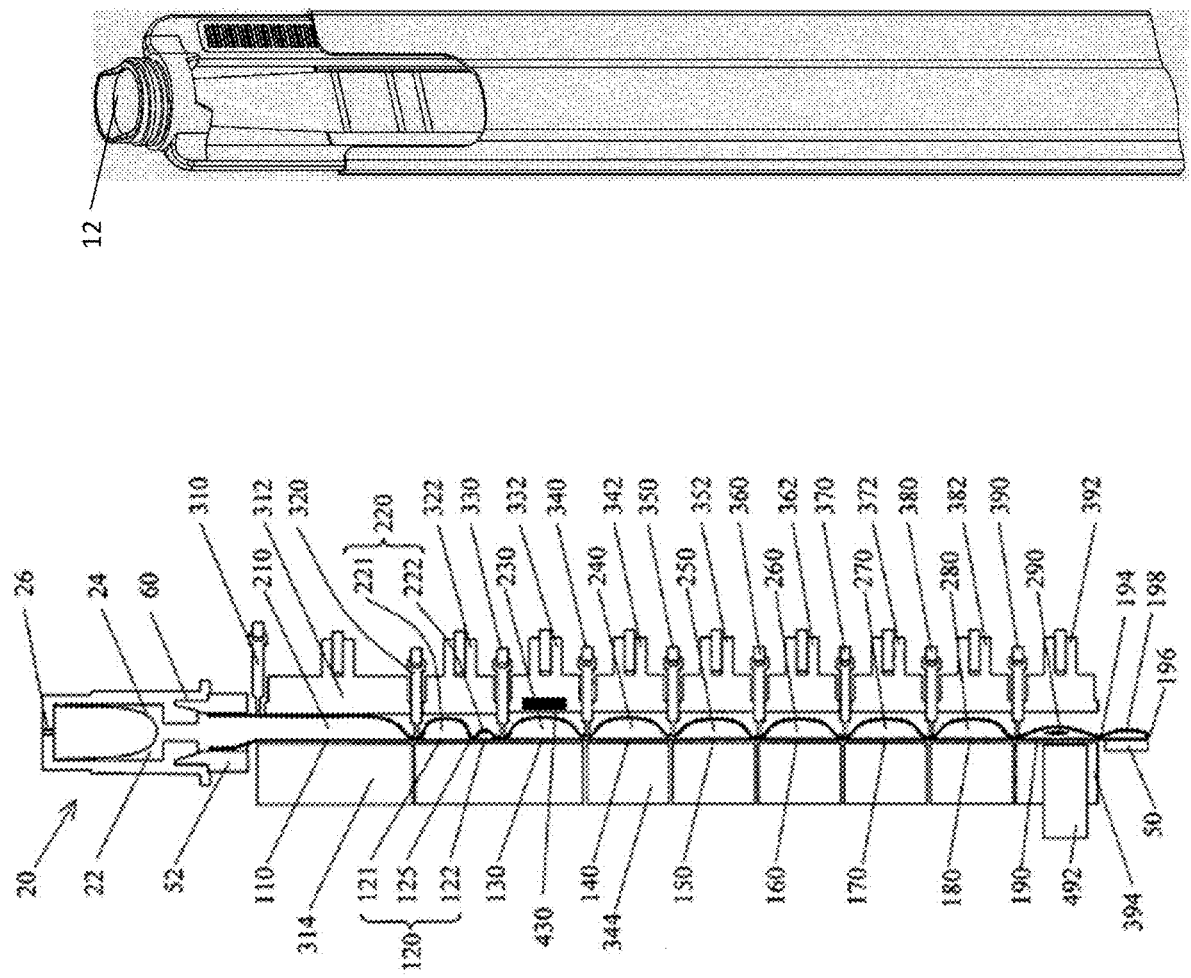
FIG. 1A is a cross sectional view of a sample tube positioned inside an analyzer.
FIG. 1B is a perspective view of an exemplary embodiment of a sample tubule.

Unless otherwise defined herein, scientific and technical terms used in connection with the present disclosure shall have the meanings that are commonly understood by those of ordinary skill in the art. Further, unless otherwise required by context, singular terms shall include pluralities and plural terms shall include the singular. The articles "a" and "an" are used herein to refer to one or to more than one (i.e., to at least one) of the grammatical object of the article. By way of example, "an element" means one element or more than one element.

The methods described herein are implemented in a sample processing device configured to perform a nucleic acid amplification technique. Nucleic acids extracted from the biological samples may be further processed by amplifying the nucleic acids using at least one of the following exemplary methods: polymerase chain reaction (PCR), rolling circle amplification (RCA), ligase chain reaction (LCR), transcription mediated amplification (TMA), nucleic acid sequence based amplification (NASBA), and strand displacement amplification reaction (SDAR). In some embodiments, the nucleic acids extracted from the organism can be ribonucleic acids (RNA) and their processing may include a coupled reverse transcription and polymerase chain reaction (RT-PCR) using combinations of enzymes such as Tth polymerase and Taq polymerase or reverse transcriptase and Taq polymerase. In some embodiments, nicked circular nucleic acid probes can be circularized using T4 DNA ligase or Ampligase™ and guide nucleic acids, such as DNA or RNA targets, followed by detecting the formation of the closed circularized probes after an in vitro selection process. Such detection can be through PCR, TMA, RCA, LCR, NASBA or SDAR using enzymes known to those familiar with the art.

In exemplary embodiments, the amplification of the nucleic acids can be detected in real time by using fluorescent-labeled nucleic acid probes or DNA intercalating dyes as well as a photometer or charge-coupled device in the molecular analyzer to detect the increase in fluorescence during the nucleic acid amplification. These fluorescently-labeled probes use detection schemes well known to those familiar in the art (i.e., TaqMan™, molecular beacons™, fluorescence resonance energy transfer (FRET) probes, Scorpion™probes) and generally use fluorescence quenching as well as the release of quenching or fluorescence energy transfer from one reporter to another to detect the synthesis or presence of specific nucleic acids.

In one embodiment, the methods disclosed herein are implemented in a device comprising self-contained microscale to macroscale channels, chambers, reservoirs, detection and processing regions. The device can be a cartridge, device, container, or pouch, e.g., as described in U.S. Pat. Nos. 6,440,725; 6,783,934; 6,818,185; 6,979,424; 8,580,559; and 8,940,526, the disclosures of which are incorporated herein by reference in their entireties, as well as devices such as those available from Cepheid Corp., Idaho Technology, Inc., and/or Biofire Diagnostics, Inc.

In a specific embodiment, the methods described herein are conducted in a sample processing device such as that described in U.S. Pat. No. 7,718,421, the disclosure of which is incorporated herein by reference. Segmented devices, such as those described in U.S. Pat. No. 7,718,421, provide a convenient vessel for receiving, storing, processing, and/or analyzing a biological sample. In certain embodiments, the segmented tubule facilitates sample processing protocols involving multiple processing steps. In certain embodiments, a reagent is introduced into a segment of the tubule, sample is collected in the tubule, and the tubule then positioned in an analyzer; the analyzer may then manipulate the tubule and its contents to process the sample.

One embodiment of the sample processing tubule is shown in FIGS. 1A-1B. The tubule includes a linear arrangement of 2 or more tubule segments 110, 120, 130, 140, 150, 160, 170, 180, and/or 190. A linear arrangement facilitates moving the sample and resultant waste and target through the tube in a controlled manner. A biological sample can be input through a first opening 12 in a first segment 110 of the tubule. Thereafter, waste from a processed sample can be moved back toward the first opening while the target is pushed towards the opposite end, thereby minimizing contamination of the target by reaction inhibitors that may have become attached to the tubule wall, and confining the target to a clean segment of the tubule which can contain suitable reagents for further operations of the target. Some embodiments may use a plurality of at least three segments, each containing at least one reagent. In some embodiments, these segments may contain reagents in the following order: the reagent in the second segment may be either a lysis reagent, a dilution or wash buffer, or a substrate; the reagent in the third segment may be either a substrate, a lysis reagent, a washing buffer or a neutralization reagent; the reagent in the fourth segment may be a wash buffer, a suspension buffer, an elution reagent, or nucleic acid amplification and detection reagents. In some embodiments, the three segments may be arranged continuously, while in other embodiments, these three segments may be separated by another segment or segments in between.

Figure 2C:
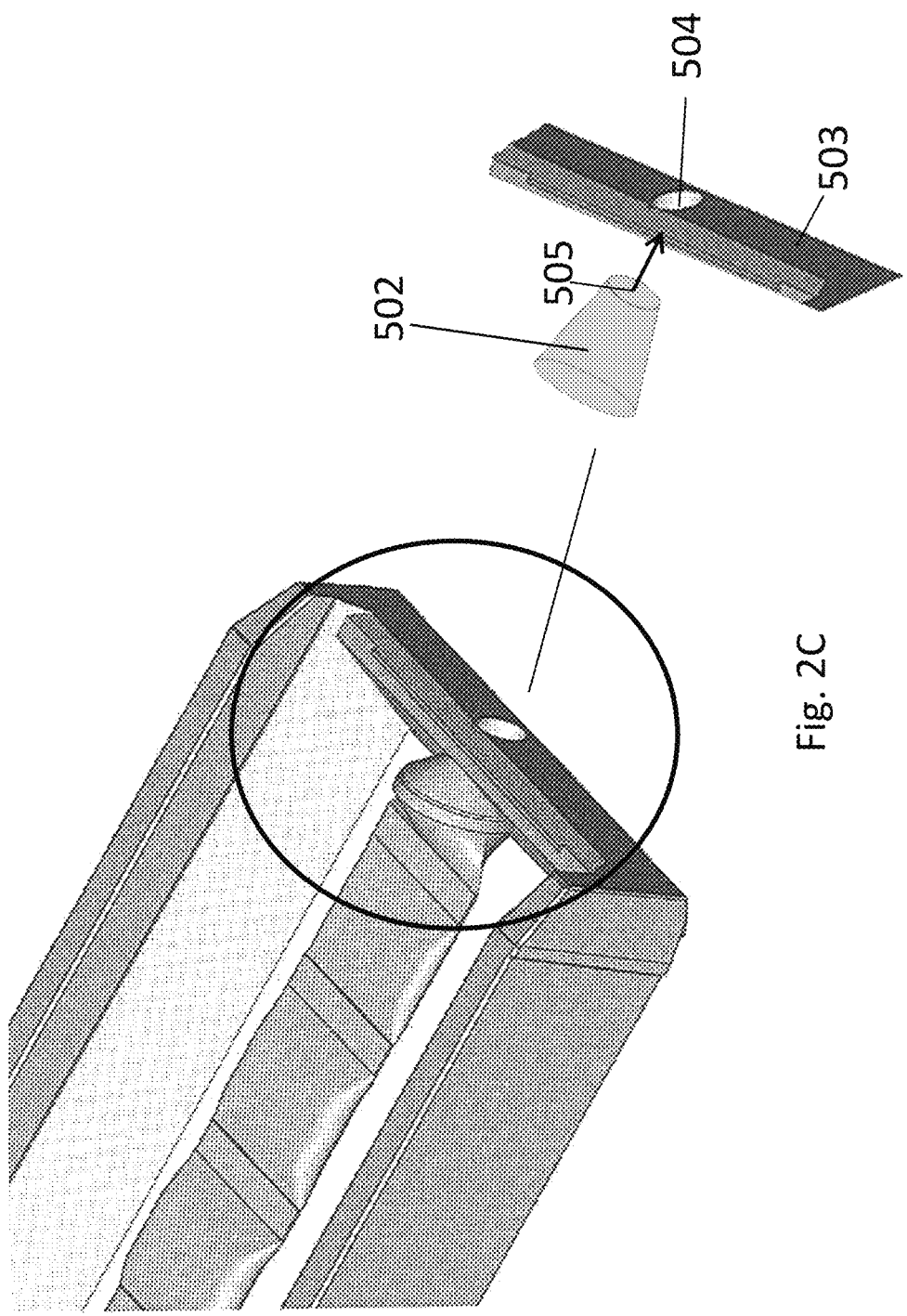
FIG. 2C is an enlarged view of the joint between the reagent introduction port and the frame of the tubule.

In a particular embodiment, a pressure gate or a breakable seal 194 can be incorporated to selectively close and open a reagent introduction port located at the distal end of the tubule to allow reagents to be introduced through the port in the segment adjacent the port. Thereafter, the pressure gate or seal is closed and the tubule can be further processed. The reagent introduction port is shown in FIGS. 2A-2C. In some embodiments, a combination of a breakable seal and a pressure gate may be provided for transferring the contents of the reagent introduction port to the adjacent segment. In a specific embodiment, the reagent introduction port is unidirectional and includes a check valve to prevent backward flow of liquid.

As shown in FIGS. 2A-2B, the tubule 500 comprises a frame 501 to which the tubule is mounted. In a particular embodiment, the reagent introduction port 502 is fixedly mounted to a base 503 of the frame and the reagent introduction port is accessed through an opening 504 in the base. An enlarged view of the reagent introduction port is shown in FIG. 2B. The reagent introduction port can be any suitable opening in a segment of the tubule into which a reagent can be added. For example, the reagent introduction port can be a septum, a luer taper connection, a frangible seal, or a mechanical valve. If the reagent introduction port is a septum, fluid can be added by piercing the septum with a needle or pipette tip and introducing the reagent into a segment of the tubule. If the reagent introduction port is a luer taper connection, a frangible seal, or a mechanical valve, the port is opened and reagent is introduced and deposited into the desired segment of the tubule.

There are two varieties of luer taper connections: locking and slipping. Luer lock fittings are securely joined by means of a tabbed hub on the female fitting which screws into threads in a sleeve on the male fitting. Luer lock connectors include one-piece luer locks and two-piece luer locks or rotating collar luer locks. One-piece luer locks come as a single mold and locking is achieved by rotating the entire luer connector or system. In two-piece luer locks, a free rotating collar with threads is assembled to the luer and locking is achieved by rotating the collar. A frangible seal is one that is easily broken, torn, or cut, including but not limited to, a blister pack or a foil seal. In one embodiment, the frangible seal is resealable or self-sealing. Alternatively, the port can be a mechanical valve, including but not limited to, a stopcock, check valve, diaphragm valve, gate valve, globe valve, needle valve, pinch valve, piston valve, plug valve, etc.

In some embodiments, a tube closing device for closing the tube after sample input may include a cap 20 (FIG. 1B) and/or clamp 310. An interface or adaptor 52 between the cap and the first opening of the flexible tubule may be used to ensure a secure, hermetic seal. In an exemplary embodiment, this interface may be threaded and may include tapered features 62 on the cap and/or a suitably rigid tube frame 50 such that, when fastened together, the threads 64 can engage to mate the tapered features 62 between the tube frame and cap to provide a suitable lock.

A substantially rigid frame 50 may be provided to hold the flexible tubule 10 suitably taut by constraining at least the proximal and distal ends of the tubule. In an exemplary embodiment, a first constraint may be provided to permanently attach and seal the tubule to the frame around the first opening of the tube. This seal may be created by welding the flexible tubule to the frame using thermal and/or ultrasonic sources. Alternatively, the seal may be created using a hot-melt adhesive joint with ethylene vinyl acetate, or by making a joint using a UV cure epoxy or other adhesives. In further embodiments, the tubule may be mechanically sealed or insert-molded with the frame.

A second constraint may be provided to attach and seal the tubule to the base of the frame via the reagent introduction port. An exemplary embodiment of this second constraint is shown in FIG. 2C, wherein the reagent introduction port is substantially open and/or capable of opening. The port enables the introduction of reagents through the port into a portion 505 of the reagent introduction port that is joined to the base of the frame at the opening 504. The port can be joined to the base of the frame by any suitable method, e.g., welding using thermal and/or ultrasonic sources, hot-melt adhesive joined with ethylene vinyl acetate or by making a joint using a UV cure epoxy or other adhesive. Alternatively, a portion of the reagent introduction port can be adhered to the base of the frame using a mechanical seal or insert-molded with the frame.

The tubule, reagent introduction port, and frame materials can be optimized for joint manufacture. For example, the frame can be made of polypropylene having a lower melting point than the thinner tubule to ensure more uniform melting across one or more weld zones. To facilitate welding between the tubule and the frame, the joint area may be tapered or otherwise shaped to include energy directors or other commonly used features enhance weld performance. In an exemplary embodiment, the rigid frame can be made of any suitable plastic by injection molding with its dimensions being approximately 150 mm tall by 25 mm wide.

The reagent introduction port is engageable by a reagent insertion mechanism, e.g., a needle or pipette tip. In one embodiment, the reagent introduction port is a luer taper connection and the reagent insertion mechanism is inserted into the luer taper connection to introduce and deposit the reagent into a segment of the tubule. Alternatively, if the port is a septum, the needle or pipette tip pierces the septum to introduce and deposit the reagent into a segment of the tubule.

The reagent insertion mechanism is inserted into the segment immediately adjacent the reagent introduction port. After reagent is introduced into the adjacent segment, the port is sealed, and the reagent is transported, if necessary, to one or more additional segments of the tubule. In one embodiment, the reagent insertion mechanism is inserted into the segment immediately adjacent the reagent introduction port, the reagent is added to the adjacent segment, the mechanism is withdrawn and the port is closed, and the tube is inverted to move the deposited reagent into a region of the tube distal from the reagent introduction port. The segment comprising the deposited reagent can be sealed using an external sealing device, and optionally, one or more additional reagents are deposited by repeating the foregoing steps. Alternatively, once reagent is introduced into the adjacent segment, the port is sealed and the tubule can be inserted into an analyzer to enable the fluid transport mechanisms within the analyzer, described in more detail below, to move the deposited reagent to another segment(s) of the tubule.

In some embodiments, a method of adding reagents to a tubule that is then processed is contemplated. In certain embodiments, the sequence of events may include, e.g., 1) introducing reagent into a segment via the reagent introduction port, and optionally moving the deposited reagent to one or more additional segments of the tubule, followed by tube sealing; 2) optionally, biological sample collection with a collection tool, 3) placing the collected sample into a flexible tubule, which can include a plurality of segments that may contain the reagents required during the test, 4) capturing target organisms or nucleic acids present in the sample using at least one substrate positioned in the tubule that may be set at a controlled temperature and/or other suitable conditions for target capture during a set incubation period, 5) removal of organisms or molecules in the unprocessed sample by transferring liquid to a waste reservoir, 6) storing waste, in a waste reservoir, that can be segregated from the target by a clamp and/or actuator compressed against the tubule, 7) adding a wash buffer, released from another segment of the tubule, to remove reaction inhibitors, 8) adding an elution reagent, from another segment, that can release the target bound to the substrate after incubation at a controlled temperature, and 9) detecting nucleic acids by techniques well known to those familiar in the art.

While the foregoing description illustrates a nucleic acid amplification workflow performed in a sample processing tubule, the tubule can also be configured to perform immunoassays, and it can also be adapted to process a sample and/or library in any suitable assay or process, including but not limited to, immunoassay detection or high throughput sequencing. The number, dimensions, and contents of the chambers/segments in the tubule can be adjusted or modified based on the desired application without departing from the spirit or scope of the application.

As shown in FIG. 1A, some embodiments may incorporate the use of a test tube 1, with a flexible tubule 10 divided into a plurality of segments, such as segments 16, 110, 120, 130, 140, 150, 160, 170, 180, and/or 190, that may be transverse to the longitudinal axis of the tubule, and which may contain reagents, such as reagents 210, 221, 222, 230, 240, 250, 260, 270, 280, and/or 290; as well as an analyzer, that may have a plurality of actuators, such as actuators 312, 322, 332, 342, 352, 362, 372, 382, and/or 392, clamps, such as clamps 310, 320, 330, 340, 350, 360, 370, 380, and/or 390, and blocks, for example 314, 344, and/or 394 (others unnumbered for simplicity); opposing the actuators and clamps, to process a sample. Various combinations of these actuators, clamps, and/or blocks may be used to effectively clamp the tubule closed thereby segregating fluid. In exemplary embodiments, at least one of said actuators or blocks may have a thermal control element to control the temperature of a tubule segment for sample processing. The sample processing apparatus can further have at least one magnetic field source 430 capable of applying a magnetic field to a segment. The sample processing apparatus can further have a detection device 492, such as photometer or a CCD, to monitor a reaction taking place or completed within the tubule.

Fluid can be driven from one segment to the next in the tubule by compressing the device with a centrally-positioned actuator, and its flanking clamps if any, to form a flow channel. The actuators adjacent a segment or select group of segments of the tubule gently compress the segments in liquid communication with the flow-channel to generate an offset inner pressure to ensure a substantially uniform gap of the flow channel. The flanking actuators can then alternatively compress and release pressure on the device on their respective segments to generate flow at a controlled flow rate. Optional flow, pressure, and/or force sensors may be incorporated to enable closed-loop control of the flow behavior. The fluid control mechanism described herein can be used in to distribute deposited reagent into one or more segments of the device following introduction through the reagent introduction port, and it can also be used for washing, enhancing the substrate binding efficiency, and detection.

The customizable sample processing tubule described herein allows the user to analyze any target of interest using a user-selected reagent. In a specific example, the user can introduce primer(s) or probe(s) via the reagent introduction port. Therefore, the reagent that can be introduced and deposited into a segment of the tubule can be a primer, probe, or combinations thereof, and the additional segments of the tubule can include the remaining reagents required to perform an assay. For example, if the user introduces one or more primers, the probes can be pre-loaded, or vice versa. The remaining pre-loaded reagents include one or more of the following in any suitable order or segments: lysis reagent, elution buffer, wash buffer, DNase inhibitor, RNase inhibitor, proteinase inhibitor, chelating agent, neutralizing reagent, chaotropic salt solution, detergent, surfactant, anticoagulant, germinant solution, isopropanol, ethanol solution, antibody, nucleic acid probes, peptide nucleic acid probes, and phosphothioate nucleic acid probes. In embodiments where one of the reagents is a chaotropic salt solution, a preferred component is guanidinium isocyanate or guanidinium hydrochloride or a combination thereof. In some embodiments, the order in which reagents may be stored in the device relative to the opening through which a sample is input, reflects the order in which the reagents can be used in methods utilizing the tube. Alternatively, in addition to the primers and probes, the user can also add one or more of the reagents listed above via the reagent introduction port. In a specific embodiment, the sample processing tubule can be supplied from the manufacturer without any reagents pre-loaded in the tubule, or with only a limited number of reagents pre-loaded, allowing the user to customize any aspect of the assay with user-selected reagents.

In some embodiments, the sample processing tubule described herein is provided in a kit. The term "kit" refers to any manufacture (e.g., a package or a container) including at least one device comprising a tubule, as described herein for specifically amplifying, capturing, tagging/converting or detecting a target nucleic acid sequence as described herein. The kit can further include instructions for use, supplemental reagents and/or components or modules used in the method described herein or a step thereof. In some embodiments, the kit includes components for obtaining, storing, and/or preparing sample. Such components include, e.g., sterile needles and syringes, EDTA-lined tubes, buffers (e.g., for binding nucleic acid to, and elution from a matrix), RNase inhibitors, and/or DNase, etc.

In addition, the kit includes an assay processing device such as that described above and optionally, one or more components for obtaining, storing, and/or preparing sample. In a specific embodiment, the assay processing device includes various reagents required to perform the methods disclosed herein stored within one or more segments of the device.

The kit can further include controls, e.g., a polynucleotide that is wild type at the sequence to be detected, or a polynucleotide that includes the sequence to be detected.

The kit can also include additional devices such as sample tubes or vials; reaction containers (e.g., tubes, multiwell plates, microfluidic chips or chambers, etc), as well as directions for use or reference to a website.

The present application is not to be limited in scope by the specific embodiments described herein. Indeed, various modifications in addition to those described herein will become apparent to those skilled in the art from the foregoing description and accompanying figures. Such modifications are intended to fall within the scope of the claims. Various publications are cited herein, the disclosures of which are incorporated by reference in their entireties.

The invention claimed is:

1. A customizable sample processing tubule comprising, from a proximate to a distal end, an opening through which a sample is introducible, at least three segments, and a reagent introduction port fluidly connected to a distal segment of the at least three segments, wherein said reagent introduction port is positioned distal from said opening and engageable with a reagent insertion mechanism to enable the introduction and deposition of reagent into at least one of said at least three segments via the reagent insertion mechanism, wherein the reagent insertion mechanism comprises a luer taper connection comprising a luer lock or luer slip and the reagent insertion mechanism comprises a threaded syringe that can be inserted into the luer taper connection.

2. The sample processing tubule of claim 1 wherein each of the at least three segments are separated from one another and from the opening and the reagent introduction port by a breakable seal.

3. The sample processing tubule of claim 1 further comprising a frame to which the tubule is mounted.

4. The sample processing tubule of claim 3 wherein said reagent introduction port is fixedly mounted to a base of said frame and said reagent introduction port is accessed through an opening in said base.

5. The sample processing tubule of claim 1 wherein a first segment of said at least three segments comprises said reagent, wherein said reagent includes one or more of the following: primers, probes, and combinations thereof, and at least one additional segment of said at least three segments comprises additional reagents including one or more of the following: primers, probes, one or more reagents required for amplification, lysis reagent, silica-coated magnetic beads, dilution buffer, wash buffer, substrate, a neutralization reagent, an elution reagent, and combinations thereof.

6. The sample processing tubule of claim 5 wherein said reagent comprises primers and a second and/or a third segment of said at least three segments comprises one or more of the following: probes, one or more reagents required for amplification, lysis reagent, silica-coated magnetic beads, dilution buffer, wash buffer, substrate, a neutralization reagent, an elution reagent, and combinations thereof.

7. The sample processing tubule of claim 5 wherein said reagent comprises primers and probes and a second and/or third segment of said at least three segments comprises one or more of the following: a one or more reagents required for amplification, lysis reagent, silica-coated magnetic beads, dilution buffer, wash buffer, substrate, a neutralization reagent, an elution reagent, and combinations thereof.

8. A kit comprising said sample introduction tube of claim 5, and in one or more separate containers, vials, or compartments, a threaded syringe, and instructions for use.

* * * * *